United States Patent [19]
Sagstetter et al.

[11] Patent Number: 5,219,333
[45] Date of Patent: * Jun. 15, 1993

[54] BLOOD COLLECTION TUBE HOLDER

[75] Inventors: William E. Sagstetter, Denver; Alan A. Wanderer, Englewood, both of Colo.

[73] Assignee: Medical Safety Products, Inc., Denver, Colo.

[*] Notice: The portion of the term of this patent subsequent to Jun. 9, 2009 has been disclaimed.

[21] Appl. No.: 828,309

[22] Filed: Feb. 28, 1992

Related U.S. Application Data

[63] Continuation of Ser. No. 430,311, Nov. 1, 1989, Pat. No. 5,120,311.

[51] Int. Cl.$^5$ ............................................. A61F 5/28
[52] U.S. Cl. ..................................... 604/110; 604/187; 604/197; 604/198; 604/199
[58] Field of Search ............... 604/110, 187, 197, 198, 604/199, 232; 128/763

[56] References Cited

U.S. PATENT DOCUMENTS

| | | |
|---|---|---|
| 4,752,290 | 6/1988 | Schramm . |
| 4,758,231 | 7/1988 | Haber et al. . |
| 4,790,827 | 12/1988 | Haber et al. . |
| 4,813,426 | 3/1989 | Haber et al. . |
| 4,834,718 | 5/1989 | McDonald . |
| 4,840,185 | 6/1989 | Hernandez . |
| 4,900,310 | 2/1990 | Ogle, III . |
| 5,120,311 | 6/1992 | Sagstetter et al. ............... 604/110 |

Primary Examiner—Vincent Millin
Assistant Examiner—J. Doyle

[57] ABSTRACT

An insert (14) for supporting a double ended needle (94, 98) during a blood collection procedure is translatably mounted with a cylinder (12) for retracting the anterior needle (98) into the cylinder (12) on completion of the procedure to prevent needle stick while the posterior needle (94) remains continually shielded against needle stick by the insert (14). An anterior lock position stabilizes the double ended needle (94, 98) during the blood collection procedure and a posterior lock position retains both ends (94, 98) of the needle shielded. Ramps (130, 132) may be associated with the posterior lock position to prevent further translation of the insert (14) and reuse of the holder (10). For a reusable holder embodiment, the used double ended needle (94, 98) is retracted, safely enclosed and locked inside the cylinder (12). The anterior end (30) of the cylinder (12) is adapted for receiving the open end (90) of a conventional needle shield (96) to permit gripping of the needle supporting hub (92) and disengagement of the needle (94, 98) from the insert (14) without exposure to needle stick. A replacement needle may then be mounted in the insert (14) and the holder (10) reused.

10 Claims, 3 Drawing Sheets fig. 6 fig. 7 fig. 8 fig. 9

BLOOD COLLECTION TUBE HOLDER

This application is a continuation application of concurrently pending application entitled "BLOOD COLLECTION TUBE HOLDER", assigned Serial No 430,311, filed on Nov. 1, 1989 now U.S. Pat. No. 5,120,311 and describing inventions by the present inventors.

BACKGROUND OF THE INVENTION

1. Field of the Invention

The present invention relates to blood collection tube holders for use during a blood collection procedure and, more particularly, to a holder having a needle supporting insert translatable with a cylinder for shielding both ends of a double ended needle after use to prevent inadvertent needle stick.

2. Description of the Prior Art

Conventional blood collection procedures involve venipuncture to draw blood into a blood collection tube. The conventional double ended needle includes a hub having an anterior needle entending in one direction and a posterior needle extending in the other direction. The hub is treadedly engaged with an apertured threaded end of a barrel to locate the posterior needle within the barrel. The other end of the barrel is open to receive an evacuated blood collection tube having a stopper to penetrably receive the posterior needle. Upon venipuncture, the blood will flow through the needle into the blood collection tube. After at least partial fill of the blood collection tube, it may be replaced by one or more further evacuated blood collection tubes, depending upon how many samples of blood are to be drawn.

On completion of the procedure, the anterior needle is withdrawn from the patient. The manner of disposal of the needle varies, depending upon the phlebotomist, the procedure to be followed and other considerations. Whether the needle is immediately capped with a needle shield for later disposal, whether the barrel is immediately disposed with the exposed needle attached or whether the needle is immediately detached or replaced, a substantial risk of inadvertent needle stick exists.

Many incurable or fatal diseases are transmissible through contact with the blood of an infected person. A needle used during a blood collection procedure obviously contains a quantity of blood. In the event of needle stick, infection from infected blood is highly likely. Considering that inadvertent needle stick occurs frequently, the degree of exposure of medical personnel to incurable or fatal diseases is intolerably high.

Particularly in recent years, various devices have been developed to minimize the likelihood of inadvertent needle stick. These devices generally include mechanisms for shielding the anterior needle after a blood collection procedure. Many of these devices perform the function of minimizing the likelihood of inadvertent needle stick but suffer from other drawbacks. Some of the devices require a two handed operation which renders such devices unacceptable since a phlebotomist must have one hand free to perform blood collection related functions. Some of the devices are relatively complex which renders their cost too high to be acceptable to medical facility administrators, particularly if such devices are not reusable. Yet other blood collection devices are complex to operate and require substantial training in proper manipulation. Such training is difficult and expensive to implement and there exists a general resistance to adaptation or modification of existing procedures, despite an understanding of increased safety which would result.

SUMMARY OF THE INVENTION

A blood collection tube holder for use in a blood collection procedure includes an insert having one end threadedly engagable with the hub of a double ended needle. The other end of the insert is configured to receive a conventional blood collection tube for penetrable engagement with the posterior needle of the double ended needle. The insert is axially translatable within a cylinder having a collar at one end for translation of the anterior needle of the double ended needle therethrough. A leaf spring biased tab extends radially from the insert for penetrable engagement with two detent positions disposed in the cylinder and interconnected with an axially aligned slot. Translation of the tab from one detent position to the other will exteriorize or retract the anterior needle through the collar. For a single use holder, a guard in conjunction with the detent position corresponding to retraction of the anterior needle will prevent further manipulation of the tab and prevent exteriorization of the anterior needle. For a reusable holder, the collar is apertured to accommodate insertion of a conventional needle shield to permit housing of the anterior needle within the cylinder while the needle is safely enclosed and locked within the holder. Engagement of the shield with the needle hub will permit disassociation of the needle hub from the insert and accommodate withdrawal of the covered double ended needle. Accordingly, the holder can permit one handed retraction of the anterior needle on completion of the blood collection procedure to preclude inadvertent needle stick. In the reusable configuration of the holder, the needle can be removed and replaced without exposing medical personnel to the possibility of needle stick during such removal and replacement.

It is therefore a primary object of the present invention to provide a blood collection tube holder for retracting and shielding a double ended needle after completion of a blood collection procedure.

Another object of the present invention is to provide a blood collection tube holder which precludes needle stick and is sufficiently inexpensive to permit one time use.

Still another object of the present invention is to provide a reusable blood collection tube holder which reduces cost per blood collection procedure and precludes inadvertent needle stick subsequent to a blood collection procedure and during replacement of a double ended needle.

Yet another object of the present invention is to provide a wobble free inexpensive double ended needle supporting insert axially translatable within a cylinder to shield the needle against inadvertent needle stick.

A further object of the present invention is to provide a safe method for shielding the anterior and posterior needles of a double ended needle subsequent to a blood collection procedure.

A yet further object of the present invention is to provide a difficult to disassemble compact blood collection tube holder for precluding inadvertent needle stick.

A still further object of the present invention is to provide a reusable blood collection tube holder for precluding inadvertent needle stick during recapping and replacing a double ended needle.

A still further object of the present invention is to provide a method for replacing a double ended needle in a blood collection tube holder while precluding possibility of inadvertent needle stick.

A still further object of the present invention is to provide a blood collection tube needle holder adapted to accept and use a plurality of different length double ended needles and blood collection tubes.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which.

DESCRIPTION OF THE PREFERRED EMBODIMENT

Any implement or device used in a medical procedure must satisfy certain federally imposed criteria. To be saleable and therefore used, further, sometimes obvious and sometimes subtle, criteria also must be met. The latter criteria is sometimes the most difficult to satisfy since it relates to perceptions held by the affected medical community of what the device should or should not be. Furthermore, any replacement device for an element used in an existing procedure should require minimal, if any, training in its use in order for it to be embraced and accepted by the ultimate users. Finally, in the area of routine procedures, operative advantages, safety benefits or time-motion benefits may be insufficient to override even small cost increases due to the usually fixed charges for such routine procedures. Venipuncture procedures for filling blood collections tubes are undertaken daily, sometimes hundreds of times, in every physician's office, clinic and hospital. The associated training and procedures have been established and stabilized for many years. The charge for this procedure is relatively fixed and little variation due to higher equipments costs is possible. Accordingly, any blood collection tube holders developed for use in such procedure must provide advantages over existing devices of sufficient magnitude to warrant adoption of a new device and the costs of the new device must be commensurate with existing costs.

Figures 1, 2:
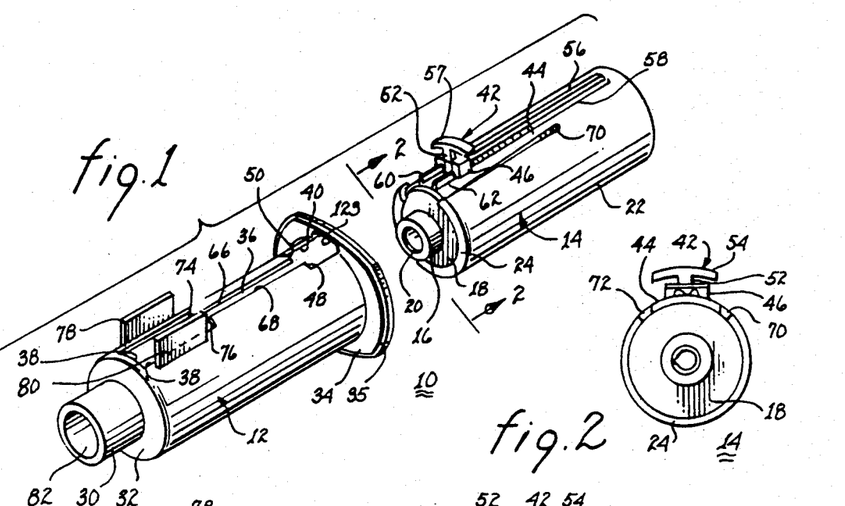
FIG. 1 is an isometric view illustrating the cylinder and the insert of a blood collection tube holder.
FIG. 2 is an end view taken along lines 2—2, as shown in FIG. 1.

Referring jointly to FIGS. 1 and 2, a two part blood collection tube holder 10 for detachably supporting the hub of a double ended needle is shown. The holder includes a cylinder 12 for axially translatably supporting an insert 14. The insert includes a hollow internally threaded boss 16 extending axially from closed end 18 of insert 14. Threads 20 in the boss are engagable with the conventional threaded hub of a double ended needle and, through such threaded engagement, firmly supports the needle. The insert includes a posteriorly extending generally cylindrical skirt 22. The axial length of the skirt is configured sufficient to house the posterior needle therein and guard against inadvertent needle stick from the posterior needle. A segment of an axially oriented annular ridge 24 extends anteriorly from closed end 18.

Cylinder 12 is generally cylindrical in configuration and includes a hollow collar 30 extending anteriorly from an annular flange 32 disposed at the anterior end of the cylinder. A retaining finger flange 34 extends radially from the posterior end of cylinder 12; this finger flange may include a ridge 35 extending along the perimeter.

An axially aligned slot 36 extends between a first circumferentially expanded slot segment 38 and a second circumferentially expanded slot segment 40. Insert 14 includes a tab 42 located generally at the anterior end of a leaf spring 44 formed as part of skirt 22. Upon mating of insert 14 with cylinder 12, tab 42 extends through slot 36 and expanded slot segments 38,40 as a function of the translational position of the insert with respect to the cylinder. To facilitate thumb access to tab 42 during exteriorization of the anterior needle in the reusable configuration of holder 10, the upper edges of wing 34 extending laterally in opposed directions from expanded slot segment 40 may be cut down or scalloped below the height of the tab.

Figure 3:
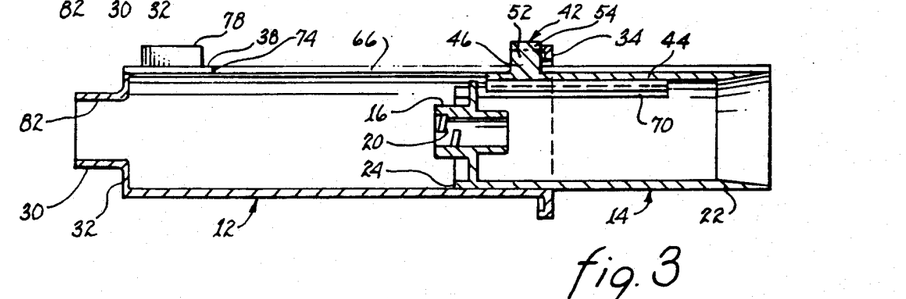
FIG. 3 is a cross sectional view illustrating the insert in the retracted position.

Referring jointly to FIGS. 1-3, insert 14 is illustrated in the needle retracted position with respect to cylinder 12. Tab 42 includes a base 46 having a lateral width approximately equivalent to the circumferential spacing of expanded slot segments 38,40. The height of the base is equal to or greater than the thickness of cylinder 12 adjacent expanded slot segments 38,40. Accordingly, the anterior edge of the base will bear against anterior edges 48,50 of expanded slot segment 40 and preclude anterior movement of the tab. Thereby, insert 14 is positionally locked with respect to cylinder 12 in the needle retracted position illustrated. A pedestal 52 extends upwardly from base 46 to support wing 54 of the tab. The lateral width of the pedestal is commensurate with the width of slot 36 to accommodate translation of the pedestal along the slot. Wing 54 extends in opposed directions from pedestal 52 a sufficient distance to prevent depression of tab 42 radially inwardly of cylinder 12, whether the tab is within slot 36, expanded slot segment 38 or expanded slot segment 40. Upon depressing tab 42 radially inwardly, resulting in radial inward bending of leaf spring 44, pedestal 52 is brought into engagement with slot 36. Upon such engagement, the tab is translatable axially along the slot resulting in commensurate rectilinear motion of insert 14. To stabilize axial translation of insert 14 within cylinder 12, a pair of axially aligned ridges 56,58 extend posteriorly from tab 42 along the leaf spring. A similar pair of ridges 60,62 may extend anteriorly of tab 42. The circumferential width defined by pair of ridges 56,58 and 60,62 is commensurate with the circumferential width between edges 66,68 of slot 36. Accordingly, the two pairs of ridges, in combination with the edges of the slot, minimize rotation about the longitudinal axis of insert 14 with respect to cylinder 12. The degree of springiness provided by leaf spring 44 is a function of, not only the material of skirt 22 of insert 14, but of the length of slot 70,72 defining the lateral edges of the leaf spring.

To translate insert 14 anteriorly with respect to cylinder 12, tab 42 is depressed radially inwardly to engage pedestal 52 with slot 36. Upon anterior translation of the tab, base 46 will ultimately become coincident with expanded slot segment 38. Upon such coincidence, the upward force exerted by leaf spring 44 will cause the base to penetrably engage anterior expanded slot segment 38. In this position, posterior axial translation of insert 14 is precluded by the rear edge of the base engaging posterior edges 74,76 of expanded slot segment 38, as illustrated in FIG. 4.

To discourage inadvertent depression of tab 42 while it is in locked engagement with expanded slot segment 38, a pair of walls 78,80 may be incorporated on opposed sides of the expanded slot segment. These walls are of a height and width commensurate with the height and width of tab 42 when the latter is in locked engagement with expanded slot 38. These walls will have the effect of shielding the tab and guarding against inadvertent depression of the tab with a resulting release of the tab from the expanded slot segment, yet access to the tab to deliberately depress it is not impeded.

Figure 4:
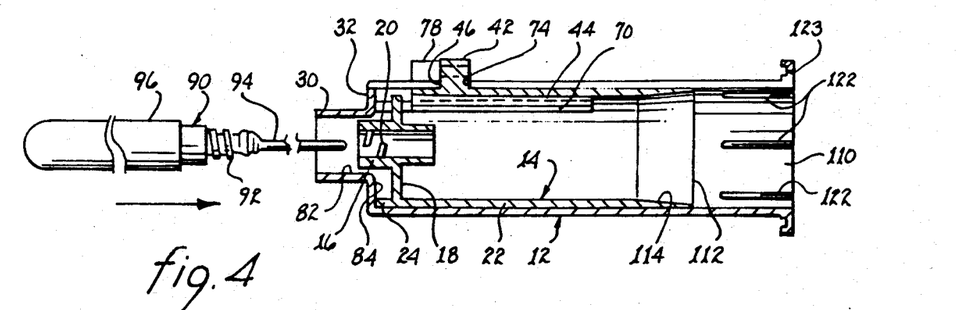
FIG. 4 is a cross sectional view illustrating the insert in the extended position for receiving a double ended needle.

Collar 30 defines a passageway 82 of sufficient diameter to accommodate partial penetration by boss 16, as shown in FIG. 4. The positional ridigity of boss 16 at the anterior end of cylinder 12 is provided by a combination of factors. First, ridge 24 of skirt 22 bears against inner surface 84 of annular flange 32 and is positionally maintained thereagainst by base 46 of tab 42 bearing against edges 74,76. Thereby, longitudinal stability of the insert with respect to the cylinder is provided. Second, the diameter of the anterior end of insert 14 proximate ridge 24 is in close tolerance with the internal anterior diameter of cylinder 12 proximate annular flange 32 to prevent lateral movement therebetween.

Segmented annular ridge 24 serves three main functions. First, it displaces the tab posteriorly to accommodate a small angle of penetration during venipuncture. Second, it displaces the contact point between the posterior needle and the blood collection tube posteriorly to provide greater gripping surface upon the blood collection tube. Third it enhances the longitudinal surface area between the insert and the cylinder.

Figure 5:
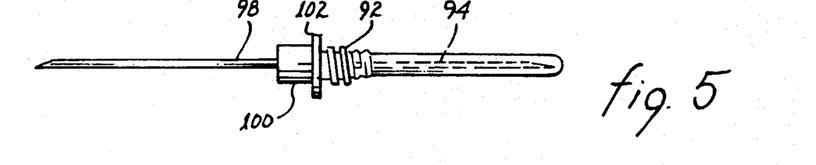
FIG. 5 is a side view of a representative conventional double ended needle.

A conventional commercially available double ended needle 90 having a threaded hub 92 is used with holder 10. To secure double ended needle 90 to holder 10, the conventional shield protecting posterior needle 94 and its associated valve is removed. Such removal will expose threaded hub 92. The posterior needle is inserted through collar 30 and boss 16 to threadedly engage the needle hub with threads 20 within the boss. The hub or the double ended needle includes an anterior needle shield support structure 100 terminated by a radially extending flange 102 for supporting a conventional shield 96. Just prior to venipuncture shield 96 is disengaged from support structure 100 and removed to expose anterior needle 98 (see FIG. 5).

As part of the blood collection procedure, a blood collection tube having a needle penetrable stopper is inserted through the open posterior end 110 of cylinder 12, through open posterior end 112 of insert 14 and into penetrable engagement with posterior needle 94. To assist and ease insertion of the blood collection tube within insert 14, the inside surface of posterior end 112 may be formed as an annular ramp 114.

On completion of the blood collection procedure and withdrawal of the last blood collection tube, a phlebotomist or other medical personnel can hold cylinder 14 in the palm of the hand and lightly grasp the cylinder with the fingers. The thumb can be used to depress tab 42 and thereafter crook the thumb to draw the tab posteriorly, as illustrated by arrow 120 in FIG. 6. The posterior movement of tab 42 will result in commensurate movement of insert 14 with respect to cylinder 12. When base 46 of tab 42 comes into correspondence with expanded slot segment 40, leaf spring 44 will urge upward movement of the tab to bring base 46 into engagement with the expanded slot segment. In the resulting position of insert 14, anterior needle 98 will have been drawn completely into the interior of cylinder 12. In this position of the anterior needle, inadvertent needle stick by the anterior needle will be impossible. The axial length of insert 14 is greater than the length of posterior needle 94 and the posterior needle will be contained completely therewithin. Thereby, inadvertent needle stick from posterior needle 94 will also be precluded by the shielding effect of skirt 22, as depicted in FIG. 6.

For manufacturing reasons, the interior surface of cylinder 12 tapers radially outwardly posteriorly. Such tapering will permit some radial movement of the anterior end of insert 14 when the insert is in the needle retracted position shown in FIG. 6. To maintain anterior needle 98 generally coincident with the longitudinal axis of cylinder 12, a plurality of tapered longitudinally extending ridges 122 are disposed internal to the posterior end of cylinder 12, as depicted in FIG. 4. A plurality of these ridges, such as 6, equiangularly spaced about cylinder 12, reduce the effective diameter of the cylinder at its posterior end into general conformance with the exterior diameter of the anterior end of insert 14. Thereby, the anterior end of insert 14 is positionally stabilized by the ridges to prevent wobble and misalignment of anterior needle 98 with the longitudinal axis of cylinder 12. Necessarily, the dimensional intrusion of tapered ridges 122 must be commensurate with the difference in diametric dimension between the posterior internal end of cylinder 12 and the external diameter of the anterior end of insert 14. Alternatively or in conjunction with ridges 122, the radial exterior of ridges 56,58 can be increased proximate tab 42 to bring about contact with arch 123 in finger flange 34 upon posterior displacement of insert 14. The resulting physical contact will reduce the likelihood of wobble and maintain the anterior needle axially aligned with the cylinder.

Figure 6:
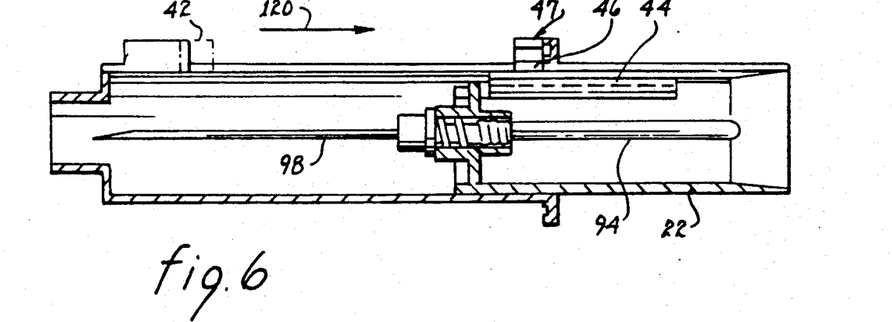
FIG. 6 illustrates retraction of the needle supporting insert.

Accordingly, in the needle retracted position shown in FIG. 6, the axial position of insert 14 with respect to cylinder 12 is stabilized by engagement of tab 42 with expanded slot segment 40. Radial stability, to prevent wobble, between the insert and the cylinder is provided by the plurality of tapered ridges engaging the circumferential surface of the anterior end of insert 14. This stability is important for two primary reasons. First, it permits aligned reextension of anterior needle 98 through passageway 82 of collar 30. Second, as will be described below, it permits capping of anterior needle 98 by sliding a needle shield through passageway 82 to cover the anterior needle.

Figure 7:
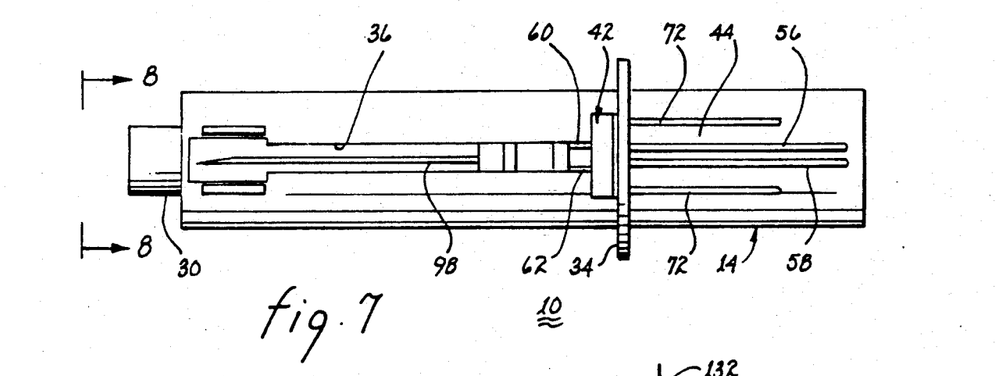
FIG. 7 is a top view illustrating the insert in the fully retracted position.
Figures 8, 9:
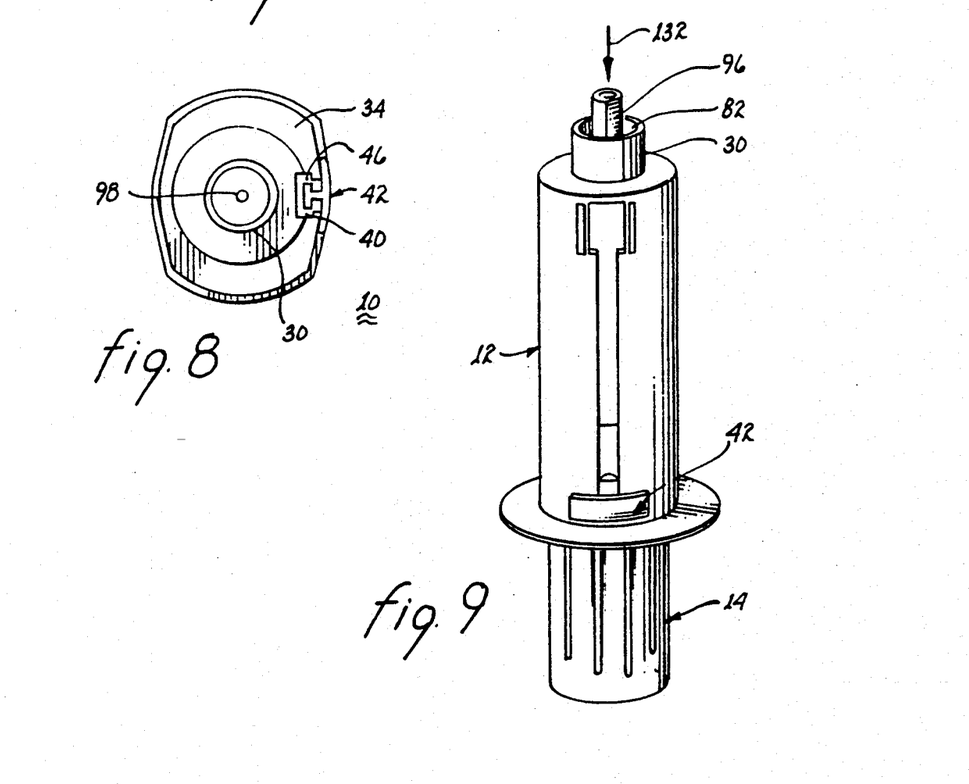
FIG. 8 is an end view taken along lines 8—8, as shown in FIG. 7.
FIG. 9 illustrates insertion of a needle shield to shield the anterior needle contained within the holder held vertically.

Referring jointly to FIGS. 7 and 8, there is shown a top view of holder 10 and an end view thereof. These views clearly illustrate leaf spring 44 extending anteriorly as part of insert 14 and defined by slits 70,72. Tab 42 has been brought posteriorly adjacent finger flange 34 to position anterior needle 98 in the retracted position. Ridges 56,58 extending radially outwardly from leaf spring 44 slidably engage slot 36, as depicted by anterior extensions 60,62 of these ridges. In the retracted position, base 46 of tab 42 is lockingly engaged within expanded slot segment 40 to preclude anterior translation of insert 14 without an accompanying depression of tab 42 to disengage the base from the expanded slot segment. As particularly noted in FIG. 8, needle 98 is essentially axially centered with passageway 82 of collar 30.

Figures 10, 12:
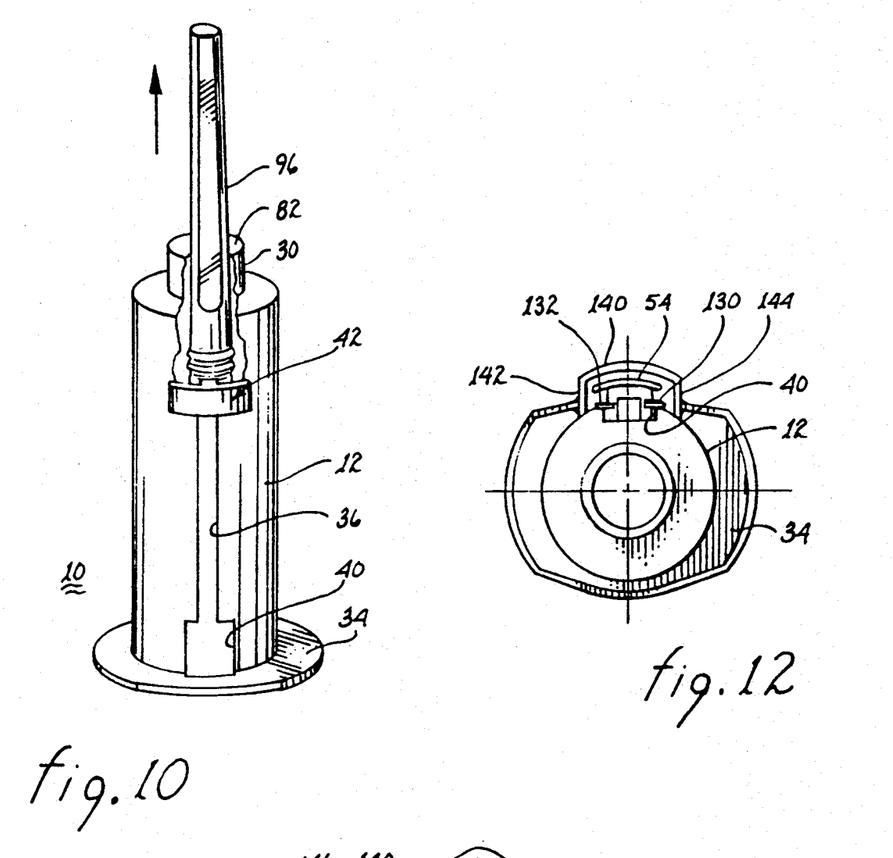
FIG. 10 illustrates steps for replacing a double ended needle.
FIG. 12 is an end view taken along lines 12—12, as shown in FIG. 11.

After completion of a blood collection procedure, holder 10 may be discarded or the holder may be reused with a replacement needle. To replace the double ended needle, a standard conventional anterior needle shield used as part of the packaging for the double ended needle is used. The open end of shield 96 is inserted through passageway 82 into cylinder 12 while tab 42 is locked in expanded slot segment 40. Continued downward movement of the shield, as depicted by arrow 132 shown in FIG. 9, will ultimately enclose the needle and the shield will come into engagement with support structure 100 of the hub of the double ended needle. For most commercially available double ended needles, the engagement of the shield with the hub is a simple press fit. At this point, a user has two options for removing the double ended needle. First, shield 96, after engaging the hub of the double ended needle, can be rotated to bring about threaded disengagement between the hub and boss 16 of insert 14. Upon such disengagement, shield 96 is withdrawn and the anterior needle will be lodged therein. Secondly, as depicted in FIG. 10, tab 42 may be translated anteriorly to extend shield 96 and the enclosed needle. With such extension, a greater gripping area of the shield will be available for a user. Accordingly, extension of the shield prior to threaded disengagement of the double ended needle from boss 16 may be more facile. After removal of the double ended needle, the posterior needle may be capped with the shield initially supplied with the double ended needle. Such capping is performed by holding shield 96 to stabilize and positionally maintain the posterior needle during capping. Holder 10 is now ready to receive a replacement needle. Collar 30 may be adapted diametrically to receive and seat the proximal end of the shield in preparation for penetration and lodgment of the anterior needle within the shield.

Figure 11:
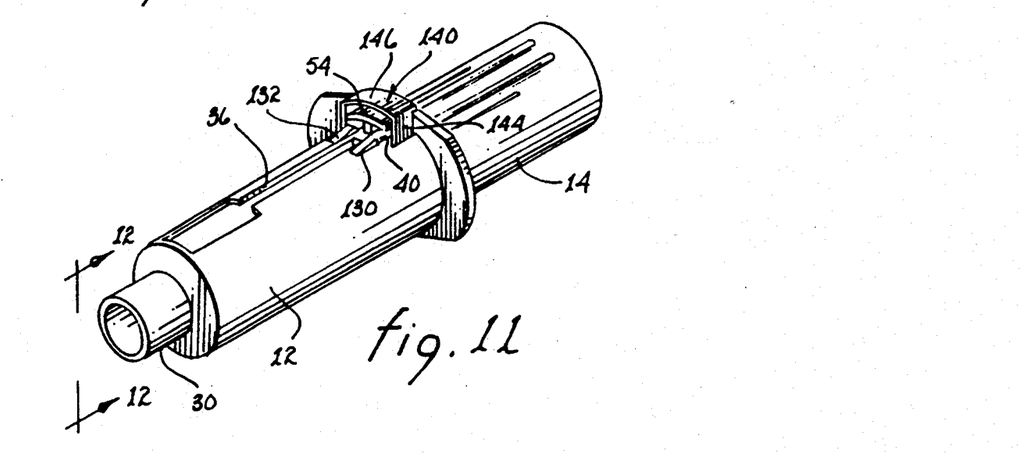
FIG. 11 illustrates a one time use embodiment of the holder shown in FIG. 1.

Under certain circumstances, it may be preferable to preclude reuse of holder 10. Such reuse can be precluded by rendering tab 42 inaccessible upon placement of the tab within expanded slot segment 40. Referring to FIGS. 11 and 12, there is illustrated a guard 140 usable for this purpose. Side walls 142,144 extend outwardly from cylinder 12 at opposed sides of expanded slot segment 40. A cover 146 interconnects the upper edges of the side walls at a location just above wing 54 of tab 42. The side walls and cover extend anteriorly from wing 34 a sufficient distance to totally enclose the tab.

When tab 42 is drawn posteriorly during retraction of the double ended needle, it will slide into guard 140. Upon entering within the guard, base 46 of the tab will become coincident with expanded slot segment 40 and due to spring action of leaf spring 44, the tab will pop up into close proximity with cover 146. In this position, the tab will be difficult to access and without extraordinary measures, the retracted double ended needle cannot be extended. Accordingly, the configuration of holder 10 illustrated in FIGS. 11 and 12 provides a non reusable blood collection tube holder. To augment difficulty in withdrawing tab 42 from within guard 140, a pair of ramps 130,132 can be formed on cylinder 12. These ramps are disposed on opposed sides of slot 36 and extend toward and terminate at anterior edges 48,50 of expanded slot segment 40. The height of these slots permits travel thereover of wing 54 during posterior travel of tab 42. Under certain circumstances, a single ramp on one side of slot 36 may be adequate. The locking feature of the ramps operates as follows. To reposition tab 42 anteriorly, the tab must be depressed to disengage, radially inwardly, base 46 from expanded slot segment 40. Such depression of the tab will lower wing 54 to a location against the butt end of the ramps. The butt end of the ramps will interfere with anterior relocation of tab 42 and the tab becomes mechanically locked within guard 140.

Cylinder 12 and insert 14 of holder 10 are manufacturable relatively inexpensively through use of molds. After manufacturing, the holder must be assembled. Such assembly is relatively easily performed in the following manner. The anterior end of leaf spring 44 of insert 14 is depressed sufficiently to permit insertion of the insert and tab within the open posterior end of cylinder 12. By axially rotating the insert when tab 42 is either proximate expanded slot segment 38 or 40, the insert is rotated about its longitudinal axis to position one end of wing 54 within the expanded slot segment. By slightly twisting the tab, the end of the wing can be made to protrude the respective expanded slot segment. Further axial rotation of the insert and commensurate depression of the cylinder along one side of the slot will permit one half of the wing to extend over the lateral edge of the expanded slot. Thereafter, the opposite wing can be popped radially outwardly and over the opposed cylindrical surface adjacent the expanded slot. By rotating insert 14 in the opposite direction, ridges 56,58 and 60,62 can be brought into alignment with slot 36 and upon such alignment, leaf spring 44 will spring radially outwardly to its quiescent position. Rectilinear translation of the insert with respect to the cylinder can now readily be effected. While disengagement of the insert from the cylinder can be accomplished by essentially reversing the above discussed procedure, such disengagement must be a very deliberate and affirmative act and is likely to result in breakage. Accordingly, during normal use of holder 10, disengagement cannot and will not come about. Test results indicate that a pulling force in the range of 25 to 40 pounds is required to disengage shield 14 from cylinder 12 due to the interference between tab 42 and finger flange 34. State of the art related blood collection tube holders come apart and expose the double ended needle upon application of a two-thirds or less pulling force. One may therefore conclude that inadvertent detachment of the insert from the cylinder will not occur during any expected use of holder 10. Holder 10 is intended to be used with commercially available sterilized double ended needles of standard configuration. The procedure attendant venipuncture does not require sterilization of holder 10. Accordingly, sterilization of a holder being manufactured may be avoided. Furthermore, since the holder does not have to be sterilized nor maintained sterile, the handling of the holder in a physician's office, clinic or hospital will require no new or different procedures. The use of holder 10 permits employment of standard venipuncture procedures except for one small modification. At the venipuncture site or shortly thereafter and before the medical personnel releases the holder, tab 42 is translated by a very simple convenient thumb motion to retract the anterior needle. Thereafter, the holder may be immediately disposed of or placed on a tray for later disposal or reuse, all without creating a danger of inadvertent needle stick. The very compact size of being essentially not much longer than a standard double ended needle substantially reduces storage space requirements both prior to and during a venipuncture procedure. Furthermore, the minimal size lessens the space required of containers for disposables. The dimensions of the holder permit use of short blood collection tubes and all size commercially available double ended needles. Aside from the above discussed methods for capping or disposing the double ended needle, other methods may be exercised. While the anterior needle is exposed after use, the anterior needle may be inserted into its original cap or shield lying on a support surface. An upward hooking motion of the holder will cause the cap to slide onto the needle. Thereafter, the cap may be frictionally engaged with the needle hub to maintain the cap in place. To separate the double ended needle from the holder, the cap is turned to unthread the needle engagement between the hub and the boss of the insert and the double ended needle is withdrawn. Secondly, certain bio hazard containers include a clamp like device for gripping objects. The exposed anterior needle may be clamped in the bio hazard container and thereafter disengaged from the holder by turning the holder to unthread the needle hub from the insert. Alternatively, if the configuration of cylinder 12 permits exteriorization of the needle hub from collar 30, the needle hub may be gripped by the bio hazard device and twisted to disengage the double ended needle from the holder.

We claim:

1. A needle inserting device for penetrable insertion into a tissue and for protecting personnel against accidental needle stick, said device comprising in combination:
  a) a needle having a pointed end;
  b) means for supporting said needle, said supporting means having a unitary tab means extending outwardly from said supporting means;
  c) a housing means for axial translation of said supporting means within said housing means, thereby selectively shielding said needle, said housing means having open anterior and posterior ends and a slot disposed therein;
  d) said unitary tab means engages said slot for supporting and guiding said tab means to accommodate axial translation of said supporting means for extension of said needle outwardly through anterior end of said housing means and for retraction of said needle within anterior end of said housing means; and
  e) a positive lock means for preventing disassembly of said supporting means from said housing means, said positive lock means comprising said unitary tab means of said supporting means and said slot of said housing means, each having a lateral and longitudinal dimension, wherein one of said lateral and longitudinal dimension of said tab means is less than or equivalent to the homologous dimension of said slot and the remaining said lateral or longitudinal dimension of said tab means is greater than the remaining homologous dimension of said slot, thereby providing positive lock means for preventing translation of said tab means inwardly through said slot of said housing means to cause disassembly of said supporting means from said housing means.

2. A needle inserting device for penetrable insertion into a tissue and for protecting personnel against accidental needle stick, said device comprising in combination:
  a) a needle having a pointed end;
  b) means for supporting said needle, said supporting means including a longitudinal axis coincident with said needle and having a tab means unitary with and extending radially outwardly from said supporting means with respect to the longitudinal axis of said supporting means;
  c) a housing means for axial translation of said supporting means within said housing means, thereby selectively shielding said needle, said (guard) housing means having open anterior and posterior ends and a slot disposed therein;
  d) said tab means extends through and outwardly of said slot of said guard means; said unitary tab means engages said slot of said housing means for supporting and guiding said tab means to accommodate axial translation of said supporting means for extension of said needle outwardly from said housing means and for retraction of said needle within said housing means; and
  e) said tab means comprising unitary wing means for precluding translation of said tab means radially inwardly with respect to the longitudinal axis of said supporting means through said slot to a location completely within the inner wall of said (guard) housing means, said wing means and said slot each having a lateral and longitudinal dimension, said wing means having a longitudinal dimension less than or equivalent to the longitudinal dimension of said slot and said wing means having a lateral dimension greater than the lateral dimension of said slot to preclude translation of said wing means radially inwardly through said slot.

3. A method for assembling a needle inserting device for penetrable insertion into a tissue and for protecting personnel against needle stick, said needle inserting device comprised of a supporting means with a pointed needle and a housing means for axially translating said supporting means within said housing means and thereby selectively shielding said needle, said housing means having a longitudinal axis, anterior and posterior openings and a slot disposed therein, said supporting means including a longitudinal axis coincident with said needle and a tab unitary with said supporting means, said tab means extending radially outwardly of said supporting means in respect to the longitudinal axis of said supporting means and said tab means mounted on a flexible resilient arm extending from a posterior fixed end in said supporting means to an anterior free end in said supporting means to accommodate inward radial movement of said tab means in respect to the longitudinal axis of said supporting means, said tab means having a unitary wing with opposed ends extending in opposed directions from said tab means, wherein following assembly of said housing means onto said supporting means said opposed ends of said wing means being positioned outwardly of said housing means a distance sufficient to extend beyond the opposed axial sides of said slot to preclude translation of said wing means radially inwardly through said slot in respect to the longitudinal axis of said supporting means, said method comprising the steps of:

a) depressing said resilient arm of said supporting means to radially inwardly displace said tab means;

b) sliding the anterior end of said supporting means and the inwardly displaced tab means into the posterior opening of said housing means;

c) rotating said supporting means about to the longitudinal axis of said housing means to locate one end of said wing in penetrable engagement with said slot and in overlapping relationship with an axially aligned edge of the penetrated said slot; and    d) exteriorizing the other end of said wing means in overlapping relationship with the other opposed axially aligned edge of the penetrated slot.

4. A blood collection tube holder for use with a detachably attached double ended needle having a threaded hub from which hub extends an anterior needle and a posterior needle, said holder comprising in combination:

a) a cylinder for shielding the anterior needle against inadvertent needle stick after a venipuncture procedure, said cylinder having an open end and a necked down end defining a collar having a passageway extending therethrough in communication with the interior of said cylinder;

b) a cylindrical insert telescopingly engagable with said cylinder for shielding the posterior needle against inadvertent needle stick and for axially translating the anterior needle through said passageway and to shield the anterior needle within said cylinder, said insert having an open end for removably receiving at least a part of a blood collection tube and a necked down end having an internally threaded boss for engaging the threaded hub of the double ended needle to position the posterior needle within said insert for penetrably engaging the blood collection tube and to position the anterior needle exterior of and extending from said insert;

c) a longitudinally extending slot disposed along said cylinder;

d) a flexible resilient arm extending from a posterior fixed end in said cylindrical insert to an anterior free end of said arm in said insert, a tab means integrally part of and extending radially outwardly from the anterior free end of said arm for engaging said slot and for guiding said insert upon relative translational movement between said insert and said cylinder;

e) first detent means in said cylinder for positionally retaining said tab means relative to said slot to define the exposed position of the anterior needle and the contained position of said insert within said cylinder and second detent means in said cylinder for positionally retaining said tab means relative to said slot to define the shielded position of the anterior needle and the extended position of said insert posteriorly from said cylinder;

f) an irreversible means for preventing repositioning of said tab means to a position anterior of said second detent means; and    g) means for preventing disassembly of said insert from said cylinder, said preventing means comprising means for precluding translation of said tab radially inwardly through said slot and through each of said first and second detent means to a location completely within the inner wall of said cylinder.

5. The apparatus as set forth in claim 4 including ramp means disposed on said housing means adjacent said slot and extending radially outwardly posteriorly, said ramp means including a butt end terminating proximate said second detent means wherein said butt end of said ramp means interferes with said tab means in said second detent means, thereby preventing repositioning of said tab means to a position anterior of said second detent means.

6. The apparatus as set forth in claim 5 wherein said ramp means comprises a ramp disposed on opposed sides of said slot.

7. A blood collection tube holder for use with a detachably attached double ended needle having a hub from which hub extends an anterior needle and a posterior needle, said holder comprising in combination:

a) a cylinder for shielding the anterior needle against inadvertent needle stick after a venipuncture procedure, said cylinder having a posterior open end and an anterior open end;

b) a cylindrical insert telescopingly engagable with said cylinder for shielding the posterior needle against inadvertent needle stick and for axially translating the anterior needle relative to said cylinder to expose the anterior needle from within said cylinder, said insert having a posterior open end for removably receiving at least a part of a blood collection tube and an anterior end having a boss for engaging the hub of the double ended needle to position the posterior needle within said insert for penetrably engaging the blood collection tube and to position the anterior needle exterior of and extending from said insert;

c) a longitudinally extending slot disposed along said cylinder;

d) tab means unitary with and extending from said insert for engaging said slot and for translating along said slot to guide said insert upon relative translational movement between said insert and said cylinder;

e) first detent means in said cylinder for positionally retaining said tab means relative to said slot to define the exposed position of the anterior needle and the contained position of said insert within said cylinder and second detent means in said cylinder for positionally retaining said tab means relative to said slot to define the shielded position of the anterior needle and the extended position of said insert posteriorly from said cylinder;

f) an irreversible means for preventing repositioning of said tab means to a position anterior of said second detent means; and    g) means for preventing disassembly of said insert from said cylinder, said preventing means comprising said tab means with a unitary wing disposed radially outwardly of said cylinder, said wing has a longitudinal dimension less than or equivalent to the longitudinal dimension of any of said slot and said first and second detents and a lateral dimension greater than the lateral dimension of said slot and said first and second detent means, thereby precluding disassembly of said insert from said cylinder.

8. The apparatus as set forth in claim 7 including ramp means disposed on said housing means adjacent said slot and extending radially outwardly posteriorly, said ramp means including a butt end terminating proximate said second detent means, wherein said butt end of said ramp means interferes with said tab means in said second detent means, thereby preventing repositioning of said tab means to a position anterior of said second detent means.

9. The apparatus as set forth in claim 8 wherein said ramp means comprises a ramp disposed on opposed sides of said slot.

10. The apparatus as set forth in claim 8 with said tab means positioned in said second detent means, wherein butt end of said ramp means interferes with wing of said tab means, thereby preventing repositioning of said tab means to a position anterior of said second detent means.

* * * * *